(12) United States Patent
Faulkner et al.

(10) Patent No.: US 9,655,740 B1
(45) Date of Patent: May 23, 2017

(54) EXPANDABLE SIZER INSTRUMENT FOR SPACING VERTEBRAL BODIES

(71) Applicant: SPINE WAVE, INC., Shelton, CT (US)

(72) Inventors: Kara Michelle Faulkner, Shelton, CT (US); Edward Charles Skolnick, Norwalk, CT (US); Mary Elizabeth Stuart, Greenwich, CT (US); Thomas John Barbieri, Hamden, CT (US)

(73) Assignee: SPINE WAVE, INC., Shelton, CT (US)

( * ) Notice: Subject to any disclaimer, the term of this patent is extended or adjusted under 35 U.S.C. 154(b) by 0 days.

(21) Appl. No.: 15/141,344

(22) Filed: Apr. 28, 2016

(51) Int. Cl.
*A61B 17/02* (2006.01)
*A61F 2/44* (2006.01)

(52) U.S. Cl.
CPC ............ *A61F 2/4425* (2013.01); *A61F 2/442* (2013.01)

(58) Field of Classification Search
CPC .............. A61B 17/025; A61B 17/8858; A61B 2017/0256; A61B 2017/0268; A61F 2/4657
See application file for complete search history.

(56) References Cited

U.S. PATENT DOCUMENTS

| | | | |
|---|---|---|---|
| 3,785,462 A | 1/1974 | Coad et al. | |
| 4,640,117 A | 2/1987 | Anderson et al. | |
| 5,122,130 A | 6/1992 | Keller | |
| 5,193,649 A | 3/1993 | Lee | |
| 5,776,054 A | 7/1998 | Bobra | |
| 5,853,412 A | 12/1998 | Mayenberger | |
| 6,174,334 B1 | 1/2001 | Suddaby | |
| 6,224,604 B1 | 5/2001 | Suddaby | |
| 6,582,451 B1 | 6/2003 | Marucci et al. | |
| 6,605,105 B1 | 8/2003 | Cuschieri et al. | |
| 7,070,598 B2 | 7/2006 | Lim et al. | |
| 7,087,055 B2 | 8/2006 | Lim et al. | |

(Continued)

FOREIGN PATENT DOCUMENTS

EP 0503662 A1 9/1992

OTHER PUBLICATIONS

C. Branch, Jr., MD, et al., "Capstone PEEK Spinal System", Medtronic, IRN8553-2.0-03/029, 2009,36 pages.

(Continued)

*Primary Examiner* — Samuel Hanna
(74) *Attorney, Agent, or Firm* — Hoffmann & Baron, LLP (57) ABSTRACT

An expandable sizer instrument for distracting and spacing opposing vertebral bodies of a spine comprises an elongate hollow shaft defining a longitudinal axis and having opposed distal and proximal ends. An actuator is provided at the proximal end and an expandable distractor is provided at the distal end. An elongate push rod extends within the shaft, a proximal end of the push rod being coupled to the actuator and a distal end being coupled to the expandable distractor. The distractor comprises a lower plate immovably attached to the shaft, and an upper plate coupled to the lower plate by a linkage mechanism fully contained within the perimeter of the distractor and operable to move the upper plate away from the lower plate in an expansion direction substantially parallel to the lower plate. The linkage mechanism comprises two laterally spaced linkage pairs with a middle link disposed therebetween.

8 Claims, 5 Drawing Sheets

(56) References Cited

U.S. PATENT DOCUMENTS

| | | |
|---|---|---|
| 7,641,671 B2 | 1/2010 | Crainich |
| 7,674,265 B2 | 3/2010 | Smith et al. |
| 7,763,028 B2 | 7/2010 | Lim et al. |
| 8,277,456 B2 | 10/2012 | Pischl et al. |
| 8,317,798 B2 | 11/2012 | Lim et al. |
| 8,986,387 B1 | 3/2015 | To et al. |
| 9,186,259 B2 | 11/2015 | To et al. |
| 2003/0171813 A1 | 9/2003 | Kiester |
| 2005/0021042 A1* | 1/2005 | Marnay ............ A61F 2/4425 606/99 |
| 2008/0114367 A1* | 5/2008 | Meyer ............ A61B 17/025 606/90 |
| 2009/0182343 A1* | 7/2009 | Trudeau ............ A61F 2/4657 606/102 |
| 2009/0222089 A1* | 9/2009 | Hauri ............ A61B 17/025 623/13.13 |
| 2011/0015638 A1* | 1/2011 | Pischl ............ A61B 17/025 606/90 |
| 2012/0158061 A1* | 6/2012 | Koch ............ A61B 17/3421 606/248 |

OTHER PUBLICATIONS

Stryker, "AVS Navigator, TLIF Surgical Technique", TLNAVST10075 Sc/GS 03/12, 2012, 32 pages.

Globus Medical, "Caliber, Expandable Lumbar Fusion Device", GMTGD68 1.11, 2011, 38 pages.

\* cited by examiner

EXPANDABLE SIZER INSTRUMENT FOR SPACING VERTEBRAL BODIES

FIELD OF THE INVENTION

The subject invention relates generally to the field of instruments for spinal surgery and more particularly to an expandable sizer instrument for sizing and spacing opposing vertebral bodies.

BACKGROUND OF THE INVENTION

Spinal implants such as interbody fusion devices are used to treat degenerative disc disease and other damages or defects in the spinal disc between adjacent vertebrae. The disc may be herniated or suffering from a variety of degenerative conditions, such that the anatomical function of the spinal disc is disrupted. Most prevalent surgical treatment for these conditions is to fuse the two vertebrae surrounding the affected disc. In most cases, the entire disc will be removed, except for a portion of the annulus, by way of a discectomy procedure. A spinal fusion device is then introduced into the intradiscal space and suitable bone graft or bone substitute material is placed substantially in and/or adjacent to the device in order to promote fusion between two adjacent vertebrae.

Certain spinal devices for achieving fusion are also expandable so as to correct disc height between the adjacent vertebrae. Examples of expandable interbody fusion devices are described in U.S. Pat. No. 7,967,867, entitled "Expandable Interbody Fusion Device", which issued on Jun. 28, 2011 (the '867 Patent), U.S. Pat. No. 8,641,769, entitled "Plastically Deformable Inter-Osseous Device", which issued on Feb. 4, 2014 (the '769 Patent), U.S. Pat. No. 8,715,351, entitled "Expandable Interbody Fusion Device With Graft Chambers", which issued on May 6, 2014 (the '351 Patent), and U.S. Pat. No. 9,078,767, entitled "Expandable Spinal Interbody Fusion Device", which issued on Jul. 15, 2015 (the '767 Patent). The '867 Patent and the '351 Patent each disclose sequentially introducing in situ a series of elongate inserts referred to as wafers in a percutaneous approach to incrementally distract opposing vertebral bodies to stabilize the spine and correct spinal height, the wafers including features that allow adjacent wafers to interlock in multiple degrees of freedom. The '769 Patent discloses an expandable interbody fusion device that is plastically deformable from a smaller to a larger height in situ. The '767 patent discloses the introduction of one or more inserts into an interbody fusion device upon the expansion of the device by the creation of incremental spaces by an insertion instrument. The '867 Patent, the '769 Patent, the '351 Patent, and the '767 Patent are assigned to the same assignee as the present invention, the disclosures of these patents being incorporated herein by reference in their entirety.

With the use of expandable interbody fusion devices, it is desirable to provide an expandable trial or sizer instrument that would enable accurate sizing of the intradiscal space prior to insertion of the interbody fusion device. Certain expandable sizer instruments are known and are described in U.S. Pat. No. 8,277,456, entitled "Spinal-Column Distractor, which issued on Oct. 2, 2012, U.S. Pat. No. 7,087,055, entitled "Minimally Invasive Expanding Spacer and Method", which issued on Aug. 8, 2006, and U.S. Pat. No. 6,582,451, entitled "Device for Use in Surgery", which issued on Jun. 24, 2003. Nevertheless, there is still a need for an expandable sizer instrument that not only provides for proper spacing but that also is capable of withstanding clinically relevant axial compressive loading conditions of the spine in situ, that are particularly experienced within the intradiscal space between opposing vertebral bodies of the spine.

SUMMARY OF THE INVENTION

It is therefore an object of the invention to provide an improved expandable sizer instrument for distracting and spacing opposing vertebral bodies of the spine during surgery.

DESCRIPTION OF THE EMBODIMENTS

For the purposes of promoting and understanding the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

Figure 1:
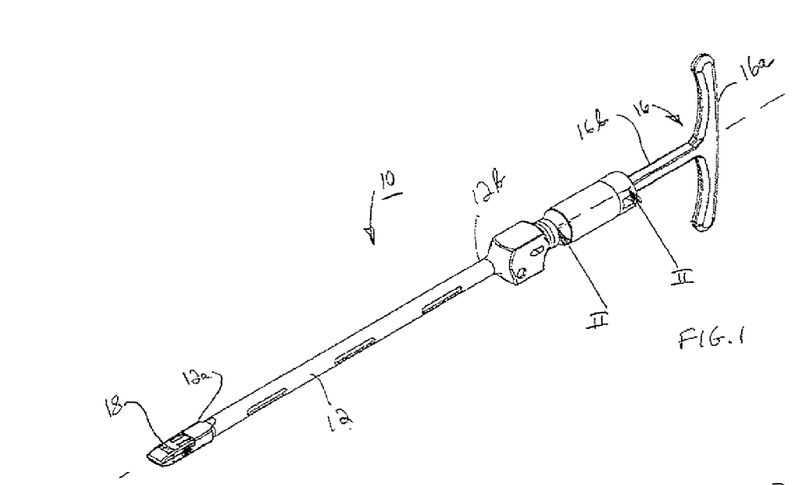
FIG. 1 is perspective view of an expandable sizer instrument for distracting and spacing opposing vertebral bodies of a spine in accordance with one arrangement of the present invention.
Figure 2:
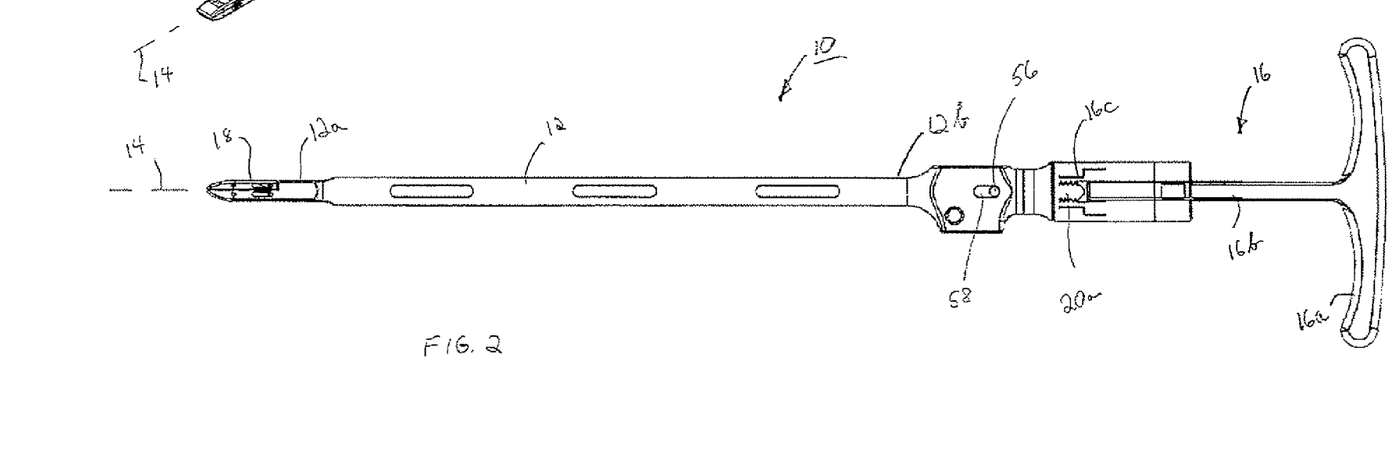
FIG. 2 is a side elevation view of the sizer instrument of FIG. 1, partially sectioned as seen along viewing lines II-II of FIG. 1.

Turning now to the drawing figures, there is shown in FIGS. 1-2 in accordance with one arrangement of the invention, an expandable sizer instrument 10 for distracting and spacing opposing body tissues, particularly vertebral bodies of a spine. Sizer instrument 10 has particular applicability in interbody fusion, as will be described, wherein opposing vertebral bodies may be distracted to a desired extent to expand the intradiscal space therebetween with the proper size interbody fusion device determined by sizer instrument 10 after expansion. Sizer instrument 10 comprises an elongate hollow shaft 12 defining a longitudinal axis 14 and having a distal end 12a and a proximal end 12b. An actuator 16 is disposed at the proximal end 12b of shaft 12 and an expandable distractor 18 is disposed at the distal end 12a of shaft 12. An elongate push rod 20 extends within and through shaft 12. A proximal end 20a of push rod 20 is coupled to actuator 16 and a distal end 20b of push rod 20 is coupled to expandable distractor 18 (see FIG. 5), as will be set forth in more detail below.

Hollow shaft 12 in one aspect comprises a generally cylindrical tube with distal end 12a being formed in a generally rectangular configuration. It should be understood however, that shaft 12 may be fully formed in a rectangular configuration or other suitable cross-section. Actuator 16 in one aspect comprises a rotatable handle 16a attached to an elongate stem 16b that is attached at the distal end to a threaded adapter 16c. Adapter 16c threadably engages threaded proximal end 20a of push rod 20 to provide a driving mechanism for axially translating push rod 20. For example, rotation of handle 16a in a clockwise direction will cause push rod 20 to move in an axial direction within shaft 12 toward the distal end 12a in a manner to actuate expandable distractor 18 in one direction, as will be described. On the other hand, rotation of handle 16a in the counterclockwise direction will cause push rod 20 to move in an opposite direction within shaft 12 toward the proximal end 12b to actuate expandable distractor 18 in an opposite direction. It should be appreciated, however, that other forms of suitable driving mechanisms, such as a trigger type arrangement may also be used to actuate distractor 18.

Turning now to FIGS. 3-7, further details of expandable distractor 18 are described. Distractor 18 comprises an upper plate 22, a lower plate 24 and a linkage mechanism 26 therebetween and coupled to upper plate 22 and lower plate 24. Upper plate 22 comprises a generally flat upper surface 22a and an opposite generally flat lower surface 22b, surfaces 22a and 22b being substantially parallel. A pair of substantially parallel and generally flat opposing side surfaces 22c and 22d extends between upper surface 22a and lower surface 22b. The distal end 22e tapers relatively smoothly downwardly from upper surface 22a toward lower surface 22b. A slot 22f extends transversely across upper plate 22 and through upper surface 22a adjacent tapered end 22e. A pair of elongated slots 22g and 22h is respectively formed through opposing side surfaces 22c and 22d, such elongated slots 22g and 22h being disposed more distally than transverse slot 22f. A pair of elongated slots 22i and 22j is formed through upper surface 22a adjacent side surface slots 22g and 22h. Slots 22i and 22j may be elongated and aligned with elongated slots 22g and 22h in side surfaces 22c and 22d, respectively, of upper plate 22. While not shown, it should be understood that similar slots may be provided through the lower surface of the lower plate 24. The purpose and function of slots 22f, 22i and 22j are set forth hereinbelow.

Lower plate 24 comprises a generally flat lower surface 24a and an opposite generally flat upper surface 24b, surfaces 24a and 24b being substantially parallel. A pair of substantially parallel and generally flat opposing side surfaces 24c and 24d extends between lower surface 24a and upper surface 24b. The distal end 24e tapers relatively smoothly upwardly from lower surface 24a toward upper surface 24b. A pair of elongated slots 24f and 24g is respectively formed through opposing side surfaces 24c and 24d, such elongated slots 22f and 22g being disposed in substantial alignment along the axial direction with slots 22g and 22h in upper plate 22.

Figure 3:
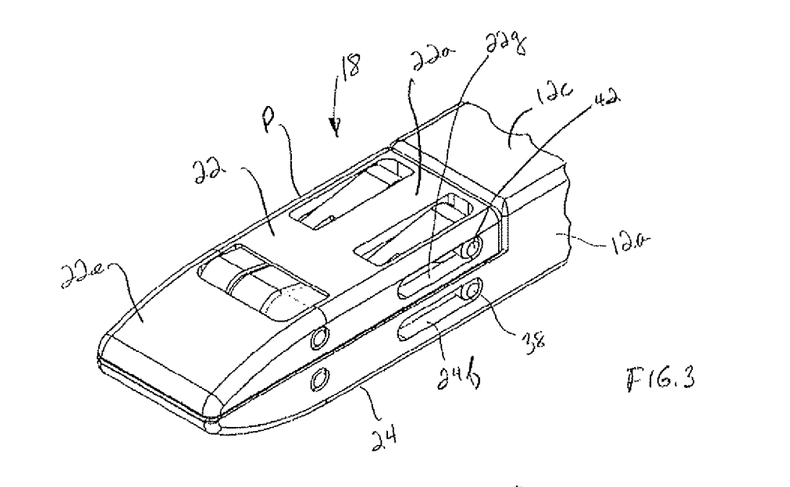
FIG. 3 is a perspective view of the distractor portion at the distal end of the expandable sizer instrument of FIG. 1 shown in an unexpanded condition.
Figure 4:
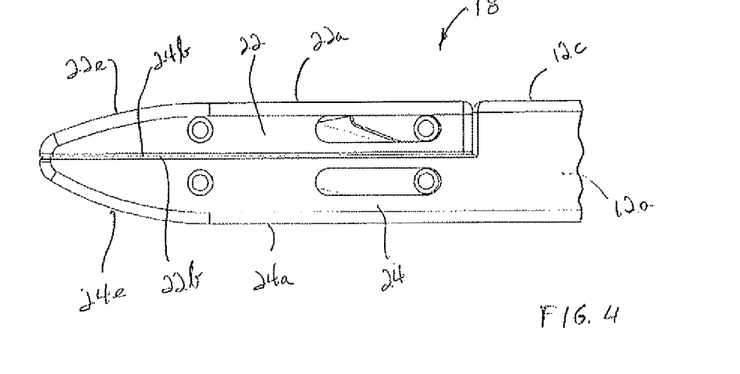
FIG. 4 is a side elevation view of the distractor portion of FIG. 3.

Lower plate 24 is rigidly and immovably attached to distal end 12a of hollow shaft 12. In one arrangement, lower plate 24 is formed as one-piece with hollow shaft 12, although lower plate 24 may be fixedly joined as a separate element to hollow shaft 12 by welding or other suitable fixation techniques. Rendering lower plate 24 immovable relative to shaft 12 of instrument 10 provides for enhanced strength during any impaction necessary to introduce distractor 18 into the intradiscal space and further stabilizes the construct during sizing and distraction since it provides a solid foundation leading to less overall motion during use. Upper plate 22 is pivotally joined to lower plate 24 as will be described in further detail below in a manner to allow upper plate 22 to move vertically away from lower plate 24 in an expansion direction with upper surface 22a and lower surface 24a remaining substantially parallel during the expansion process. Linkage mechanism 26 further permits upper plate 22 to collapse toward lower plate 24 in a manner whereby upper surface 22a is substantially coincident with or lower than an upper surface 12c of distal end 12a as illustrated in FIGS. 3-4. Further as shown in FIGS. 3-4, in the collapsed condition lower surface 22b of upper plate 22 rests on upper surface 24b of lower plate 24 to provide a generally low-profile for introduction of distractor 18 into an intradiscal space. To further enhance such introduction, tapered distal ends 22c and 24e jointly provide for a smooth gradual entry of distractor 18 into the intradiscal space prior to expansion.

Figure 5:
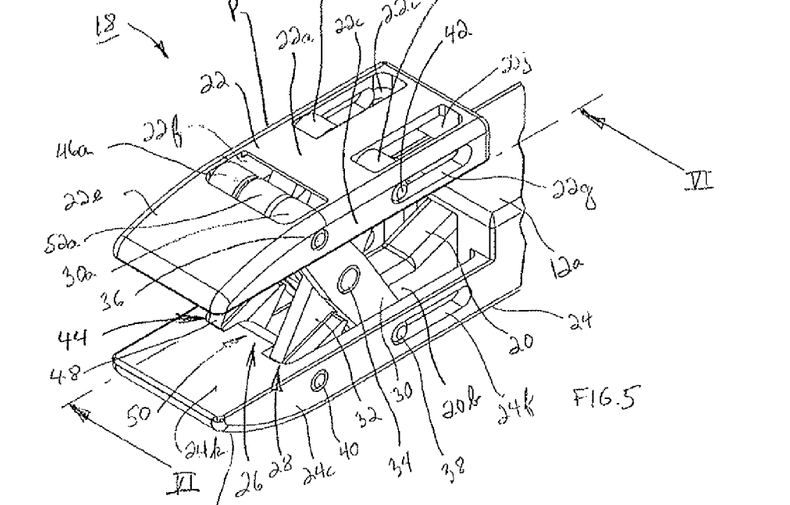
FIG. 5 is a perspective view of the distractor portion at the distal end of the expandable sizer instrument of FIG. 1 shown in an expanded condition.
Figure 6:
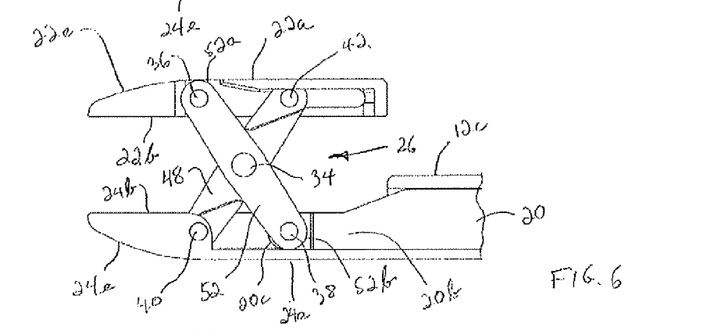
FIG. 6 is a cross-sectional view of the expanded distractor portion of FIG. 5 as seen along viewing lines VI-VI of FIG. 5.
Figure 7:
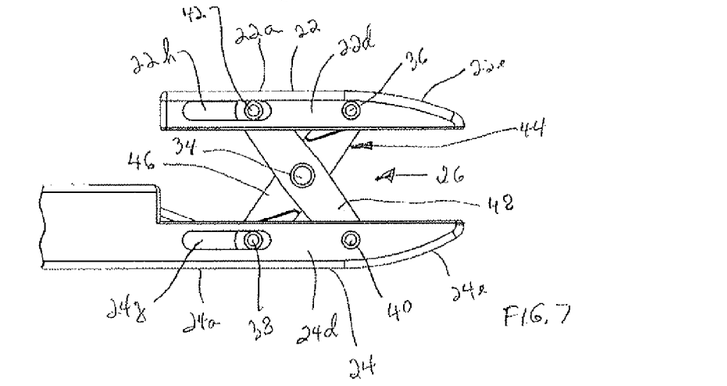
FIG. 7 is a side elevation view of the expanded distractor portion of FIG. 5 showing the side opposite the view of FIG. 5.

Referring to FIGS. 5-7, details of linkage mechanism 26 are described. Linkage mechanism 26 is configured to operate in a manner responsive to actuator 16 to move upper plate 22 away from and toward lower plate 24 in an expansion direction substantially orthogonal to longitudinal axis 14 while keeping upper surface 22a and lower surface 24a substantially parallel to each other. Linkage mechanism 26 includes a first linkage pair 28 as depicted in FIG. 5 comprising a first link 30 and a second link 32 pivotally joined to each other by a connecting pin 34 between opposite ends of links 30 and 32. One end 30a of link 30 is pivotally attached to upper plate 22 by a connecting pin 36 extending through an opening through side surfaces 22c and 22d. Opposite end of link 30 is pivotally and movably attached to lower plate 24 by a connecting pin 38 slidably movable within elongated slot 24f of lower plate 24 as distractor 18 is expanded or collapsed. One end of link 32 is pivotally attached to lower plate 24 by a connecting pin 40 extending through an opening through side surfaces 24c and 24d. Opposite end 32a of link 32 is pivotally and movably attached to upper plate 22 by a connecting pin 42 slidably movable within elongated slot 22g of upper plate 22 as distractor 18 is expanded or collapsed.

Linkage mechanism 26 further includes a second linkage pair 44 as depicted in FIGS. 5 and 7 comprising a first link 46 and a second link 48 pivotally joined to each other by connecting pin 34 which extends transversely across distractor 18 and between opposite ends of links 46 and 48. One end 46a of link 46 is pivotally attached to upper plate 22 by connecting pin 36 extending transversely across upper plate 22 and through an opening through side surfaces 22d and 22c. Opposite end of link 46 is pivotally and movably attached to lower plate 24 by connecting pin 38 extending transversely across lower plate 24 and slidably movable within elongated slot 24g of lower plate 24. One end of link 48 is pivotally attached to lower plate 24 by connecting pin 40 extending transversely across lower plate 24 and through an opening in side surface 24*d*. Opposite end 48*a* of link 48 is pivotally and movably attached to upper plate 22 by connecting pin 42 extending transversely across upper plate 22 and slidably movable within elongated slot 22*h* of upper plate 22 as distractor 18 is expanded or collapsed.

First linkage pair 28 and said second linkage pair 44 are laterally spaced along the longitudinal axis to define a space 50 therebetween. A middle link 52 is disposed within space 50 and is pivotally attached between its opposite ends to linkage pairs 28 and 44 by connecting pin 34, as shown in FIG. 6. One end 52*a* of middle link 52 is pivotally attached to upper plate 22 by connecting pin 36. Opposite end 52*b* of link 52 is pivotally and movably attached to lower plate 24 by connecting pin 38. In such arrangement, middle link 52 is oriented generally parallel to link 30 of first linkage pair 28 and link 46 of second linkage pair 44. In accordance with one aspect of the invention, middle link 52 provides enhanced stability of distractor 18 and restricts outer linkage pairs 28 and 44 from buckling during use.

As illustrated in FIG. 5, the upper end 30*a* of link 30, the upper end 46*a* of link 46 and the upper end 52*a* of middle link 52 each extends into slot 22*f* formed through and across upper surface 22*a* of upper plate 22. Similarly, the upper end 32*a* of link 32 extends into slot 22*j* and the upper end 48*a* of link 48 extends into slot 22*i*. The provision of slots 22*f*, 22*i* and 22*j* through upper surface 22*a* of upper plate 22 allows the upper ends of links 30, 46, 52, 32 and 48 to be attached to upper plate 22 as near to the upper surface 22*a* as practicable while keeping such links disposed interiorly of distractor 18. Such construction when similar slots are also formed though lower plate 24 enables a relatively low-profile of the height of distractor 18. In addition, as can been seen in FIGS. 3 and 5, the entire linkage mechanism 26 is fully contained within the perimetric boundary P defined by the perimeters of upper plate 22 and lower plate 24. By maintaining links 30, 46, 52, 32 and 48 interiorly of distractor 18, damage to surrounding tissues and nerve roots may be minimized during introduction of distractor 18 into the intradiscal space.

While middle link 52 has been described herein as being oriented in the direction illustrated in FIG. 5, wherein link 52 extends from upper plate 22 proximally toward lower plate 24, it should be appreciated that middle link 52 may also be oriented in the opposite direction. As shown in an alternative arrangement in FIGS. 8-9, middle link 52 may be oriented to extend in a direction from upper plate 23 distally toward lower plate 25. In such arrangement, middle link 52 is oriented generally parallel to link 32 of first linkage pair 28 and link 48 of second linkage pair 44. In this orientation, one end 52*a* of middle link 52 is pivotally and movably attached to upper plate 22 by connecting pin 42. Opposite end 52*b* of link 52 is pivotally attached to lower plate 24 by connecting pin 40. Such orientation may help minimize or prevent certain loading failures where such loading is significant due to the amount of compressive force experienced during sizing. In addition, slots 54*a*, 54*b*, 54*c*, 54*d* and 54*e* may be formed through upper surface 23*a* of upper plate 23 to accommodate link upper ends 30*a*, 32*a*, 46*a*, 48*a* and 52*a*, respectively to maintain a low profile height of the distractor portion, as similarly described above. Slots 54*b*, 54*d* and 54*e* may be elongated and aligned with elongated slots 22*g* and 22*h* in side surfaces 22*d* and 22*c*, respectively, of upper plate 22. The entire linkage mechanism 26 in this arrangement is also fully contained within the perimetric boundary P defined by the perimeters of upper plate 23 and lower plate 25 as shown in FIG. 8.

As illustrated in FIGS. 5 and 6, distal end 20*b* of said push rod 20 is coupled to expandable distractor 18 at connecting pin 38. In accordance with a further arrangement of the invention, the terminal end 20*c* of push rod 20 is configured to terminate adjacent the location of connecting pin 38 and does not extend axially distally beyond linkage pairs 28 and 44. As such, when the distractor 18 is in the expanded condition, push rod 20 does not completely translate the full axial extent of distractor 18. In this arrangement, the terminal end 20*c* of push rod 20 terminates between the approximate mid-point of distractor 18, defined by connecting pin 34, and the distal end 12*a* of outer shaft 12. This allows lower plate 24 to have a solid extent 24*k* of material across lower plate 24 at the distal end thereof which provides more strength and stability for distractor 18 during sizing, distraction and any impaction which may be necessary to introduce distractor 18 into the intradiscal space. Similarly, upper plate 22 may also have a solid extent across the distal end 22*e* for further enhancement of the strength of distractor 18.

Figure 8:
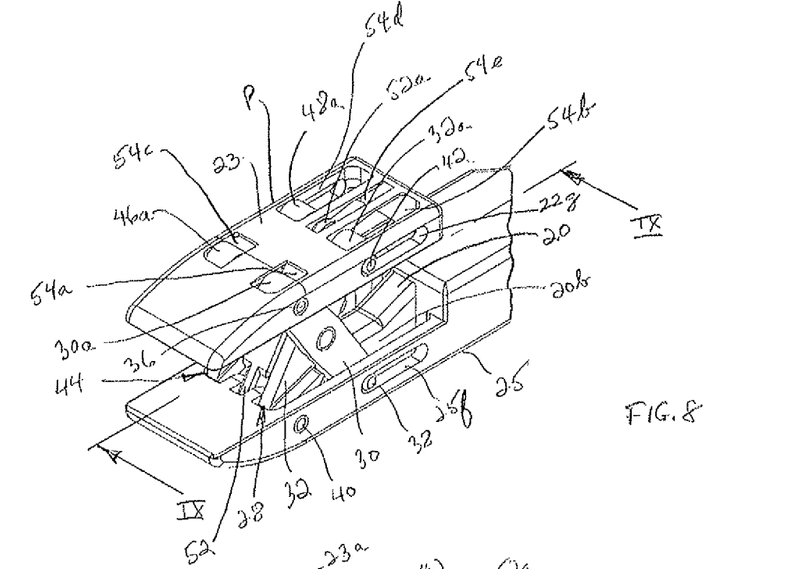
FIG. 8 is a perspective view of an alternative arrangement of the distractor portion at the distal end of the expandable sizer instrument shown in an expanded condition.
Figure 9:
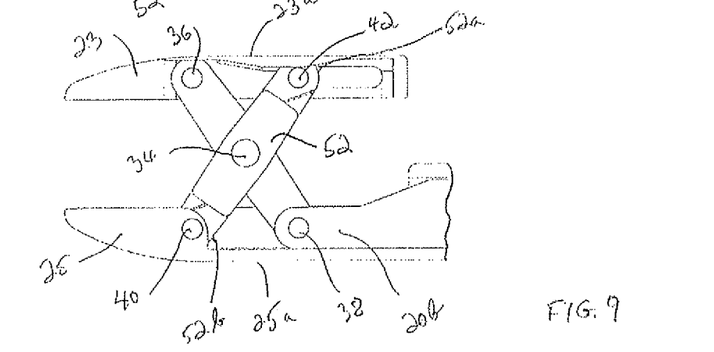
FIG. 9 is a cross-sectional view of the expanded distractor portion of FIG. 8 as seen along viewing lines IX-IX of FIG. 8.

The construction of sizer instrument 10 described heretofore with an expandable distractor 18 having a linkage mechanism with two sets of laterally spaced linkage pairs as shown in the arrangement of FIGS. 3-7 and in the alternative arrangement of FIGS. 7-8, has particular use in interbody fusion procedures as approached from a posterior or anterior direction. In such approaches, the length of distractor 18, as defined by the length of upper plate 22 or 23 may be in the range of 20-30 mm. The initial height of distractor 18 in the unexpanded, collapsed condition may be in the range of 6-10 mm and the distractor 18 may be expanded up to a height ranging from 15-21 mm. The width of such distractor 18 may be in the range of 10-30 mm. In an interbody fusion procedure, after a suitable discectomy is performed and the intradiscal space suitably prepared with conventional instruments, a sizer instrument 10 to distract opposing vertebral bodies and determine the size of an interbody fusion device is used. The tapered ends 22*e*, 24*e* of collapsed distractor 18 are placed between the vertebral bodies to introduce distractor 18 into the intradiscal space. If necessary the proximal end of instrument 10 may be impacted with an appropriate mallet or the like to properly position distractor 18 into the intradiscal space. Once in position, the surgeon rotates handle 16 in a clockwise direction to thereby drive push rod 20 distally. Such distal movement of push rod 20, which is attached to connecting pin 38, actuates linkage mechanism 26 and causes expansion of distractor 18 and distraction of opposing vertebral bodies by moving upper plate 22 or 23 vertically upward and away from lower plate 24 or 25, respectively. During expansion of distractor 18, connecting pins 38 and 42 slide within slots 24*f*, 24*g* and 22*g*, 22*h*, respectively, from the proximal position shown in FIG. 3 distally to the position shown in FIG. 5. Distraction is continued by clockwise rotation of handle 16 until distractor 18 has been expanded to its maximum anatomic extent when the spine has reached ligamentotaxis. As a safety precaution, axial translation of push rod 20 may be limited by a mechanical stop comprising a pin 56 as shown in FIG. 2 attached to push rod 20 that encounters the end of a slot 58 formed at proximal end 12*b* of shaft 12. After the desired height is achieved the surgeon can determine the correct size of the interbody fusion device to be implanted. Suitable indicia or gradations may be provided on sizer instrument 10 as a measurement of the expanded height of distractor 18. Distractor 18 may then be collapsed by counterclockwise rotation of handle 18 causing push rod 20 to move proximally thereby actuating linkage mechanism 26 and drawing upper plate 22 toward lower plate 24. Sizer instrument 10 is then removed from the intradiscal space.

Figure 10:
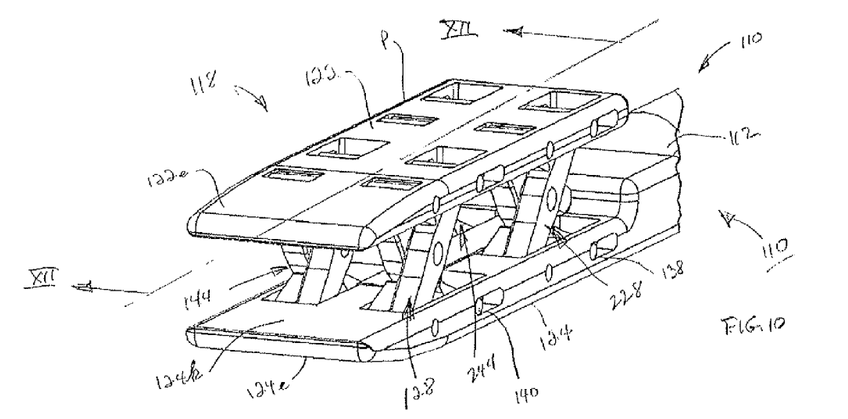
FIG. 10 is a perspective view of further arrangement of the distractor portion at the distal end of the expandable sizer instrument shown in an expanded condition.
Figure 11:
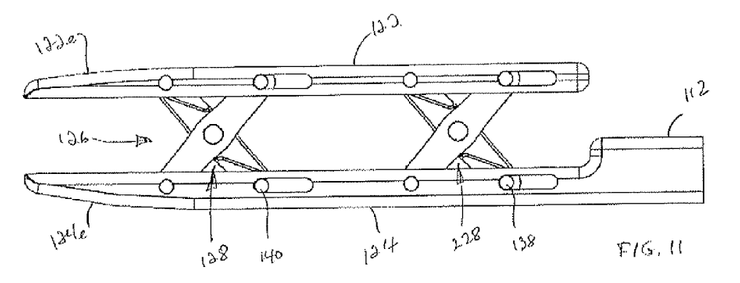
FIG. 11 is a side elevation view of the expanded distractor portion of FIG. 10.
Figure 12:
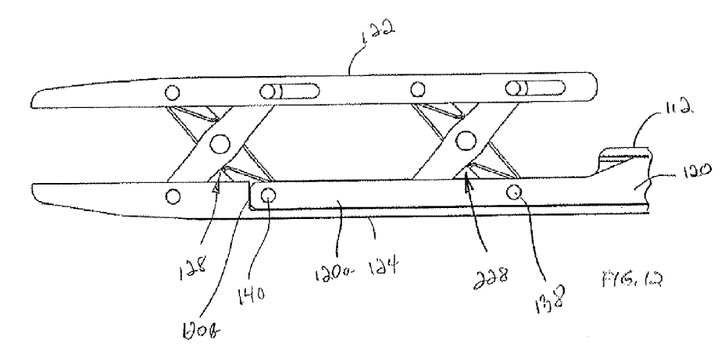
FIG. 12 a cross-sectional view of the expanded distractor portion of FIG. 10 as seen along viewing lines XII-XII of FIG. 10.

Having described sizer instrument 10 for use in posterior and anterior interbody fusion procedures, it should be appreciated that an alternative sizer instrument 110 may be used for lateral interbody fusion where longer interbody fusion devices are typically implanted from an approach along the lateral direction. As shown in FIGS. 10-12, sizer instrument 110 is constructed in a manner similar to sizer instrument 10, except that expandable distractor 118 disposed at the distal end of sizer instrument 110 is configured to be longer than expandable distractor 18 to provide distraction and sizing for longer lateral interbody fusion devices under different loading conditions.

Distractor 118 comprises an upper plate 122, a lower plate 124 and a linkage mechanism 126 therebetween and coupled to upper plate 122 and lower plate 124. Unlike linkage mechanism 26 which has two sets of laterally spaced linkage pairs 28, 44 as described above with reference to FIGS. 3-7, linkage mechanism 126 comprises four sets of linkage pairs including laterally spaced distal linkage pairs 128, 144 and laterally spaced proximal linkage pairs 228, 244. Linkage pairs 128 and 144 are disposed adjacent the distal ends 122e, 124e of upper plate 122 and lower plate 124, respectively. Linkage pairs 228 and 244 are longitudinally spaced from linkage pairs 128, 144 and are disposed more proximal to outer shaft 112. Linkage pairs 128, 144 and 228, 244 are attached to upper plate 122 and lower plate 124 with links and connecting pins similar to the connection of linkage pairs 28, 44 to upper plate 22 and lower plate 24, as described hereinabove. Although not shown, distractor 118 may be configured to include a middle link, such as link 52, between distal linkage pairs 128, 144 and/or between proximal linkage pairs 228, 244, depending upon the anticipated load to be handled by distractor 118.

An elongate push rod 120, similar to rod 20, extends within and through shaft 112. Push rod 120 has a proximal end (not shown) coupled to an actuator similar to actuator 16 and a distal end 120a that is coupled to expandable distractor 118. Connecting pin 138 pivotally and movably couples proximal linkage pairs 228 and 244 to lower plate 124 while connecting pin 140 pivotally and movably couples distal linkage pairs 128 and 144 to lower plate 124. The distal end 120a of push rod 120 is pivotally coupled to connecting pin 138. Distal end 120a may also be extended to pivotally couple to connecting pin 140. As such, terminal end 120b of push rod 120 is configured to terminate adjacent connecting pin 140 and does not extend axially distally beyond distal linkage pairs 128 and 144. Accordingly, push rod 120, like push rod 20, whether coupled only to connecting pin 138 or also to connecting pin 140, or both, does not completely translate the full axial extent of distractor 118. This allows lower plate 124 to have a solid extent 124k of material across lower plate 124 at the distal end 124e which provides more strength and stability for distractor 118 during sizing, distraction and any impaction which may be necessary to introduce distractor 118 into the intradiscal space. Upper plate 122 may also have a solid extent across the distal end 122e for further enhancement of the strength of distractor 118. Further, as with the previous arrangements, the entire linkage mechanism 126 is fully contained within the perimetric boundary P defined by the perimeters of upper plate 122 and lower plate 124 as shown in FIG. 10. In use, axial movement of push rod 120 in the distal direction directly actuates both distal linkage pairs 128, 144 and proximal linkage pairs 228, 244 to expand distractor 118. In all other respects, and except as noted herein, lateral sizer instrument 110 operates and is constructed the same as sizer instrument 10. In a particular arrangement, the length of distractor 118, as defined by the length of upper plate 122 may be in the range of 35-60 mm. The initial height of distractor 118 in the unexpanded, collapsed condition may be in the range of 6-10 mm and the distractor height may be expanded up to a range of 15 mm-21 mm. The width of such distractor 118 may be in the range of 15-30 mm. It should be understood that the dimensions set forth herein of distractors 18 and 118 are illustrative, and that other dimensions to suit a particular application may be provided.

In one arrangement, the components of sizer instrument 10 and 110 are made of stainless steel and/or stainless steel alloys. It should be appreciated, however, that other suitable materials may be used in the construction of these instruments. The upper and lower surfaces of distractors 18 and 118 may also be coated with a titanium nitride or other suitable material to enhance the strength of the distractors 18, 118 at the interfaces with the vertebral bodies.

While the invention has been illustrated and described in detail in the drawings and foregoing description, the same should be considered as illustrative and not restrictive in character. For example, sizer instrument 10 may be configured such that upper surface 22a and lower surface 24a of upper plate 22 and lower plate 24, respectively, are disposed at an angle so as to distract opposing vertebral bodies in a lordotic manner. It is understood that only the preferred embodiments have been presented and that all changes, modifications and further applications that come within the spirit of the invention are desired to be protected.

What is claimed is:

1. An expandable sizer instrument for distracting and spacing opposing vertebral bodies of a spine, comprising:
    an elongate hollow shaft defining a longitudinal axis and having a distal end and a proximal end;
    an actuator at the proximal end of said elongate hollow shaft;
    an expandable elongate distractor having a distal end and a proximal end, said elongate distractor being disposed at the distal end of said elongate hollow shaft;
    an elongate push rod extending within said hollow shaft, a proximal end of said push rod being coupled to said actuator and a distal end of said push rod being coupled to said expandable distractor;
    said elongate expandable distractor comprising:
        a lower plate immovably attached at its proximal end to said hollow shaft, an upper plate coupled to said lower plate by a first linkage pair operable to move said upper plate away from and toward said lower plate in an expansion direction substantially orthogonal to said longitudinal axis while maintaining the upper plate to be substantially parallel to said lower plate in a manner to selectively and lockably increase or decrease a maximum height of said expandable elongate distractor,
        said lower plate comprising an upper surface and an opposing lower surface configured to contact one of the opposing vertebral bodies, and a pair of opposite side surfaces connecting the upper and opposing lower surfaces of the lower plate to each other, the distal end of said lower surface of said lower plate tapering relatively smoothly upwardly toward the opposing upper surface of said lower plate, said upper plate comprising an upper surface configured to contact the other one of the opposing vertebral bodies and an opposing lower surface, and a pair of opposite side surfaces connecting the upper and opposing lower surfaces of the lower plate to each other, the distal end of said upper surface of said upper plate tapering relatively smoothly downwardly toward the opposing lower surface of said upper plate, at least one slot extending through said upper surface and said lower surface of said upper plate, an outside perimeters of said upper plate and said lower plate defining a perimetric boundary of said elongate expandable distractor, said first linkage pair being fully contained within the perimetric boundary of said distractor, said first linkage pair comprising a first link and a second link each having opposite ends respectively, said first link and said second link being pivotally joined to each other at intermediate portions between said opposite ends by a first connecting pin, wherein one end of said first link is pivotally attached to said lower plate by a second connecting in extending through openings in said pair of opposite side surfaces of said lower plate and said opposite end of said first link is pivotally and movably attached to said upper plate by a third connecting pin extending through elongated slots in said pair of opposite side surfaces of said upper plate aligned with the longitudinal axis, and wherein one end of said second link is pivotally attached to said upper plate by a fourth connecting pin extending through openings in said pair of opposite side surfaces of said upper plate with said one end of said second link being accommodated in and fully contained within said at least one slot and disposed interiorly of the perimetric boundary of said distractor, and wherein said opposite end of said second link is pivotally and movably attached to said lower plate by a fifth connecting pin extending through elongated slots in said pair of opposite side surfaces of said lower plate aligned with the longitudinal axis, said distal end of said push rod being attached to said fifth connecting pin, such that axial movement of the push rod relative to the hollow shaft selectively and lockably increases and decreases the maximum height of said elongate distractor;

a second linkage pair cooperative with said first linkage pair, said second linkage pair being fully contained within said perimetric boundary of said distractor and being spaced laterally from said first linkage pair relative to said longitudinal axis thereby defining a space between said first linkage pair and said second linkage pair, said second linkage pair comprising a third link and a fourth link each having opposite ends respectively, said third link and said fourth link being pivotally joined to each other at intermediate portions between said opposite ends by said first connecting pin, wherein one end of said third link is pivotally attached to said lower plate by said second connecting pin and said opposite end is pivotally and movably attached to said upper plate by said third connecting pin, and wherein one end of said fourth link is pivotally attached to said upper plate by said fourth connecting pin with said one end of said fourth link being accommodated in and fully contained within said at least one slot and disposed interiorly of the perimetric boundary of said distractor, and wherein said opposite end of said fourth link is pivotally and movably attached to said lower plate by said fifth connecting pin;

a middle link disposed within said space defined between said first and second linkage pairs, said middle link being pivotally joined to said first linkage pair and said second linking pair at an intermediate portion between opposite ends of said middle link by said first connecting pin, one end of said opposite ends of said middle link being pivotally attached to said upper plate by said fourth connecting in and the other end of the opposite ends being pivotally attached to said lower plate by said fifth connecting pin, said middle link being generally parallel to one of said first link or said second link; and     wherein the first and second linkage pairs and the middle link are fully contained within the elongated distractor between the opposite side surfaces of the upper and lower plates and between the upper surface of the upper plate and the lower surface of the lower plate.

2. The expandable sizer instrument of claim 1, wherein said fifth connecting pin extends transversely across said lower plate and into the elongated slots in said opposite side surfaces of said lower plate.

3. The expandable sizer instrument of claim 2, wherein said second connecting pin extends transversely across said upper plate and into the elongated slots in said opposite side surfaces of said upper plate.

4. The expandable sizer instrument of claim 1, wherein said actuator comprises a threaded driving mechanism and a rotatable handle.

5. The expandable sizer instrument of claim 4, wherein rotation of said handle in one direction moves said push rod in the distal direction to operate said linkage mechanism and move said upper plate in the expansion direction away from said lower plate.

6. The expandable sizer instrument of claim 5, wherein rotation of said handle in a direction opposite said one direction moves said push rod in the proximal direction to operate said linkage mechanism and move said upper plate in the expansion direction toward said lower plate.

7. The expandable sizer instrument of claim 1, wherein said third link is generally parallel to said first link, and said middle link is generally parallel to both of said first link and said third link.

8. The expandable sizer instrument of claim 1, wherein said fourth link is generally parallel to said second link, and wherein said middle link is generally parallel to both of said second link and said fourth link.

\* \* \* \* \*